United States Patent
Van Vaals

(10) Patent No.: US 6,768,917 B1
(45) Date of Patent: Jul. 27, 2004

(54) MAGNETIC RESONANCE IMAGING METHOD AND SYSTEM

(75) Inventor: Johannes Jacobus Van Vaals, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 09/857,310

(22) PCT Filed: Sep. 26, 2000

(86) PCT No.: PCT/EP00/09484

§ 371 (c)(1), (2), (4) Date: Jun. 1, 2001

(87) PCT Pub. No.: WO00/09484

PCT Pub. Date: Apr. 12, 2001

(30) Foreign Application Priority Data

Oct. 1, 1999 (EP) .............................. 99203204

(51) Int. Cl.[7] ............................. A61B 5/05; G01V 3/00
(52) U.S. Cl. ...................... 600/424; 600/423; 600/412; 324/315
(58) Field of Search ............................... 600/424, 423, 600/412, 410, 420, 421; 324/315, 318, 307, 309, 314, 313, 312, 311, 310; 606/41

(56) References Cited

U.S. PATENT DOCUMENTS

| | | | | |
|---|---|---|---|---|
| 5,378,987 A | | 1/1995 | Ishihara et al. | 324/315 |
| 5,711,300 A | * | 1/1998 | Schneider et al. | 600/412 |
| 5,730,129 A | * | 3/1998 | Darrow et al. | 600/407 |
| 5,938,599 A | * | 8/1999 | Rasche et al. | 600/410 |
| 5,938,600 A | * | 8/1999 | Van Vaals et al. | 600/411 |
| 5,964,705 A | * | 10/1999 | Truwit et al. | 600/423 |
| 6,026,316 A | * | 2/2000 | Kucharczyk et al. | 600/420 |
| 6,061,587 A | * | 5/2000 | Kucharczyk et al. | 600/411 |
| 6,064,206 A | * | 5/2000 | Van Vaals et al. | 324/312 |
| 6,272,370 B1 | * | 8/2001 | Gillies et al. | 600/411 |
| 6,298,259 B1 | * | 10/2001 | Kucharczyk et al. | 600/411 |
| 6,377,834 B1 | * | 4/2002 | Zhou et al. | 600/412 |
| 6,626,902 B1 | * | 9/2003 | Kucharczyk et al. | 606/41 |

FOREIGN PATENT DOCUMENTS

| WO | WO 99/21024 A1 | * | 4/1999 |
|---|---|---|---|
| WO | WO 01/25810 A1 | * | 4/2001 |

* cited by examiner

*Primary Examiner*—Diego Gutierrez
*Assistant Examiner*—Tiffany A. Fetzner
(74) *Attorney, Agent, or Firm*—John Vodopia

(57) ABSTRACT

A method of forming a magnetic resonance image involves separate measurement of the position of a measuring site. The magnetic resonance image is corrected on the basis of the measured position of the measuring site.

13 Claims, 3 Drawing Sheets

MAGNETIC RESONANCE IMAGING METHOD AND SYSTEM

The invention relates to a magnetic resonance imaging method. In order to form a magnetic resonance image of an object, the object is arranged in a steady, as uniform as possible magnetic field. Often only a part of the object is imaged; to this end, the part of the object to be imaged is then arranged in the steady magnetic field. The steady magnetic field orients spins in the object to be examined predominantly in the direction of the steady magnetic field. According to such a magnetic resonance imaging method, spins in an object to be examined are excited. Relaxation of the excited spins produces magnetic resonance signals which are acquired. A magnetic resonance image is reconstructed from the magnetic resonance signals acquired.

A magnetic resonance imaging method of this kind is known from U.S. Pat. No. 5,378,987.

The known magnetic resonance imaging method is dedicated notably to measurement, on the basis of the magnetic resonance signals, of a temperature distribution in the object to be examined. The cited United States patent deals with the problems caused by displacements of the object to be examined. The cited United States patent mentions notably that the measured temperature distribution may be spoiled by displacement of the object to be examined. The known magnetic resonance imaging method offers a rather cumbersome, time-consuming solution to this problem. The known magnetic resonance imaging method notably necessitates the execution of separate magnetic resonance excitation sequences for the detection of displacements of the object and for the measurement of the frequency shift due to variation of the temperature, referred to as "chemical shift data", respectively. According to the known magnetic resonance imaging method, such magnetic excitation sequences must both be repeated for different values of the echo time in the measurement of the chemical shift.

It is an object of the invention to provide a magnetic resonance imaging method wherein it is comparatively simply achieved that hardly any disturbances occur due to motions of the object to be examined.

This object is achieved by means of a magnetic resonance imaging method according to the invention wherein
  magnetic resonance signals are acquired,
  the position of a measuring site is determined, and
  the magnetic resonance image is reconstructed from the magnetic resonance signals and on the basis of the position of the measuring site.

In accordance with the invention, the position of a measuring site is separately determined, such a position can be separately measured. Furthermore, a predetermined geometrical relationship exists between the measuring site and the region reproduced in the magnetic resonance image. On the basis of the position determined for the measuring site, disturbances due to motion of the object to be examined can be avoided in the magnetic resonance image on the basis of the predetermined geometrical relationship between the measuring site and the region to be imaged (FIG. 3 step 320). The object to be examined is a patient. During the acquisition of the magnetic resonance signals, the patient is liable to move and/or motions are liable to occur within the body of the patient, due to the respiration and/or the heartbeat. The magnetic resonance imaging method according to the invention notably ensures that hardly any disturbances which are due to such motions in and/or of the patient occur in the magnetic resonance image.

The invention is implemented in such a manner that a selected slice of the object to be imaged contains the measuring site. Notably when images of the same slice are repeatedly formed it is achieved that the same slice is always accurately reproduced. It is then ensured that the selected slice always extends through the measuring site. The selection of such a slice is performed on the basis of an RF excitation in combination with a selection gradient. Such a selection gradient is superposed on the steady magnetic field.

The magnetic resonance image can also be accurately corrected for motion in and/or of the object on the basis of the measured position of the measuring site and the predetermined geometrical relationship between the measuring site and the region to be imaged.

It has been found that the position of the measuring site can be readily determined. As a result, disturbances in the magnetic resonance image which are due to motion can be very simply counteracted.

These and other aspects of the invention will be elaborated on the basis of the following embodiments which are defined in the dependent claims.

Preferably, a clearly recognizable detail of the object to be examined and an indication of the measuring site are reproduced in the magnetic resonance image. This is realized by reproducing the relevant detail and the measuring site together in the magnetic resonance image (FIG. 3 step 380). On the basis of the predetermined geometrical relationship between the measuring site and the relevant detail, the correct position of the reproduction of the detail relative to the indication of the measuring site in the magnetic resonance image can also be derived (FIG. 3 step 390). On the basis of the derived correct position of the detail it can then be readily checked whether the position of the detail has shifted due to motion in and/or of the object and, if desired, the position of the detail in the magnetic resonance image can be corrected.

The magnetic resonance imaging method according to the invention is particularly suitable for accurately deriving the local temperature distribution in the object to be examined by means of the magnetic resonance imaging method. To this end, reference magnetic resonance signals are first acquired at a predetermined reference temperature, after which measuring magnetic resonance signals are acquired at a locally increased temperature in the object to be examined. A reference magnetic resonance image of the part of the object to be examined is reconstructed from the reference magnetic resonance signals. A measuring magnetic resonance image of the part of the object to be examined is reconstructed from the measuring magnetic resonance signals for which the temperature has locally been varied (FIG. 3 step 370). The temperature variation causes a frequency shift of the measuring magnetic resonance signals relative to the reference magnetic resonance signals; this frequency shift will be referred to as "temperature dependent chemical shift". The measuring site is reproduced in the reference magnetic resonance image as well as in the measuring magnetic resonance image and the position of the measuring site is separately reproduced so as to be suitably recognizable in the reference magnetic resonance image and the measuring magnetic resonance image, or is separately measured (FIG. 3 step 380). Furthermore, the predetermined geometrical relationship between the reproduction of the detail and the indication of the measuring site in the reference magnetic resonance image is also determined on the basis of the reference magnetic resonance image. As a result, the measuring magnetic resonance image and the reference magnetic resonance image can be made to register, the same details in both images then being situated in the same position in the images relative to the indication of the measuring site in both images. It is thus achieved that the local temperature variation can be accurately derived from the frequency shifts of the measuring magnetic resonance signals relative to the reference magnetic resonance signals while avoiding disturbances due to motion. The determination of the local variation of the temperature on the basis of the temperature dependent chemical shift (FIG. 3 step 350) per se is rather sensitive to motion, because the measuring magnetic resonance signals are spatially encoded on the basis of the frequencies of these signals. Because a separate determination or measurement of the position of the measuring site is available according to the invention, the effect of the temperature dependent chemical shift can be separated from the frequency encoding of the position in space whereto the magnetic resonance signals relate.

The registration of the measuring magnetic resonance image with the reference magnetic resonance image, will be better as the positions of more different details in the measuring magnetic resonance image are corrected.

The measuring magnetic resonance image is preferably made to register with the reference magnetic resonance image by counteracting disturbances due to motions during the formation of the measuring magnetic resonance image. Disturbances due to motion can be counteracted according to the invention by ensuring, on the basis of the position determined for the measuring site, that the reference magnetic resonance signals and the measuring magnetic resonance signals relate to or originate from the same region of the object to be examined. This can be readily achieved by selecting, on the basis of the measuring site, the same slice of the object for the acquisition of the reference magnetic resonance signals as well as for the acquisition of the measuring magnetic resonance signals. Thus, prior to the reconstruction of the reference magnetic resonance image and the measuring magnetic resonance image it is already ensured that these two magnetic resonance images register.

It is also possible to make the reference magnetic resonance image and the measuring magnetic resonance image register after the reconstruction from the reference magnetic resonance signals and the measuring magnetic resonance signals. The measuring site is preferably chosen to be such that the indication of the measuring site is situated in substantially the same positions in the reference magnetic resonance image and the measuring magnetic resonance image. The shift of the reproduction of the detail in the measuring magnetic resonance image relative to the reproduction of the same detail in the reference magnetic resonance image then follows from the relative position of the reproduction of the same detail in the reference magnetic resonance image and the measuring magnetic resonance image relative to the indication of the measuring site.

It is a further object of the invention to provide a magnetic resonance imaging method enabling accurate measurement of the temperature distribution in the object to be examined.

This object is achieved by means of a method of forming a magnetic resonance image wherein:

magnetic resonance signals are acquired, the position of a measuring site is measured, and the temperature at the measuring site is derived from the magnetic resonance signals. Because the position of the measuring site is separately measured, the effect of the frequency shift of the magnetic resonance signals (the temperature dependent chemical shift), caused by the temperature variation, can be separated from the frequency encoding of the spatial positions whereto the magnetic resonance signals relate. It is notably possible to derive the local temperature at the exact position of the measuring site from the magnetic resonance signals. The effect of motion of and/or in the object to be imaged, i.e. the patient to be examined, is notably reduced.

Preferably, a set of reference magnetic resonance signals is acquired at a predetermined reference temperature (FIG. 3 step 330). When the local temperature within the body of the patient to be examined is derived by means of the method according to the invention, the reference temperature is the body temperature of the patient to be examined. Subsequently, the temperature is locally increased and a set of measuring magnetic resonance signals is acquired at the increased temperatures (FIG. 3 step 340). Because the position of the measuring site has been separately measured, the temperature dependent chemical shift can be derived from the frequency shift of the measuring magnetic resonance signals relative to the reference magnetic resonance signals, (FIG. 3 step 350) so that the local temperature can be determined at the measuring site (FIG. 3 step 350). Because the position of the measuring site has been separately measured, the accuracy of the determination of the temperature will hardly be affected when motion of and/or in the patient to be examined occurs between the acquisition of the reference magnetic resonance signals and the measuring magnetic resonance signals. Furthermore, the position of the measuring site at which the local temperature increase is measured is particularly reliable and notably is hardly affected by motions of and/or in the patient to be examined.

Further advantages are achieved by deriving the temperature distribution in the object to be examined on the basis of the measuring magnetic resonance signals, the reference magnetic resonance signals and the position of the measuring site determined. Preferably, this temperature distribution is reproduced as a thermal image. Brightness or color values represent the local temperature in such a thermal image. Furthermore, such a thermal image also contains image information concerning the anatomy of the patient. This image information is acquired by means of magnetic resonance imaging methods which are known per se. Such a temperature distribution constitutes a useful technical aid notably for performing thermal treatment on the body of the patient. Such thermal treatments concern (laser) ablation of tissue. Laser radiation is then used to destroy diseased tissue by local heating. The diseased tissue in the desired region can be readily locally thermally treated on the basis of the temperature distribution reproduced in the thermal image.

It has been found that a microcoil is particularly suitable for determining the position of the measuring site. The microcoil is introduced into the body of the patient (FIG 3 step 300). The microcoil receives magnetic resonance signals practically exclusively from the immediate vicinity of the microcoil (FIG. 3 step 310). The magnetic resonance signals received by the microcoil thus accurately represent the current position of the microcoil. The location where the microcoil is situated thus constitutes the measuring site. Microcoils for interventional e.g. endocavitary applications are smaller than approximately 1 cm. Generally speaking, microcoils having dimensions of between 0.5 mm and 3 mm are used, but even smaller microcoils, being smaller than 1 mm or even as small as approximately 0.1 mm, are also used to determine the position of the measuring site particularly accurately. The microcoil is preferably used in conjunction with an energy-dissipating element. Such an energy-dissipating element locally deposits energy in the form of laser radiation, in the tissue so as to increase the local temperature. The microcoil is preferably arranged near the energy-dissipating element. Furthermore, the microcoil is advantageously used in combination with a temperature sensor. Use is preferably made of a temperature sensor in the form of a fiber thermometer. Such a fiber thermometer has hardly any disturbing effect on the magnetic resonance signals. Preferably, the temperature sensor is arranged in the immediate vicinity of the microcoil. This enables separate measurement of the temperature in the direct vicinity of the microcoil. The temperature distribution relative to the temperature measured at the measuring site can be derived on the basis of the position of the measuring site as determined by the microcoil and the temperature at the measuring site as determined by the temperature sensor.

The invention also relates to a magnetic resonance imaging system. The magnetic resonance imaging system according to the invention is arranged to determine the position of the measuring site. Preferably, the magnetic resonance imaging system according to the invention is provided with the microcoil. Using the microcoil, magnetic resonance signals representing the position of the measuring site are acquired at the area of the measuring site or in the immediate vicinity of the measuring site. Such a microcoil enables measurement of the position of the measuring site with an accuracy of less than 1 mm and even 0.1 mm. This accuracy is dependent inter alia on the accuracy of measurement of the temperature and the phase of the position magnetic resonance signals. It is also advantageous to use a plurality of microcoils, preferably two or three microcoils. When two microcoils are used, the position and the direction of the line through the microcoils can be measured; when three microcoils are used (not in one line), the position and the orientation of the plane through the three microcoils can be measured (FIG. 3 step 320). It is also possible to use an even larger number of microcoils in order to measure deformations in the anatomy of the patient. The magnetic resonance image can be corrected for the measured deformation by image processing on the basis of the measured deformations.

The invention also relates to a computer program. The computer program according to the invention contains instructions for the acquisition of magnetic resonance signals, for the determination of the position of the measuring site, and for the reconstruction of the magnetic resonance image from the magnetic resonance signals on the basis of the position of the measuring site determined. The magnetic resonance imaging system includes a computer for executing the various functions of the magnetic resonance imaging system. When the computer program according to the invention is loaded into the computer of the magnetic resonance imaging system, the method according to the invention can be carried out by means of the magnetic resonance imaging system.

These and other aspects of the invention are apparent from and will be elucidated, by way of non-limitative example, with reference to the embodiment described hereinafter and the accompanying drawing; therein:

Figure 1:
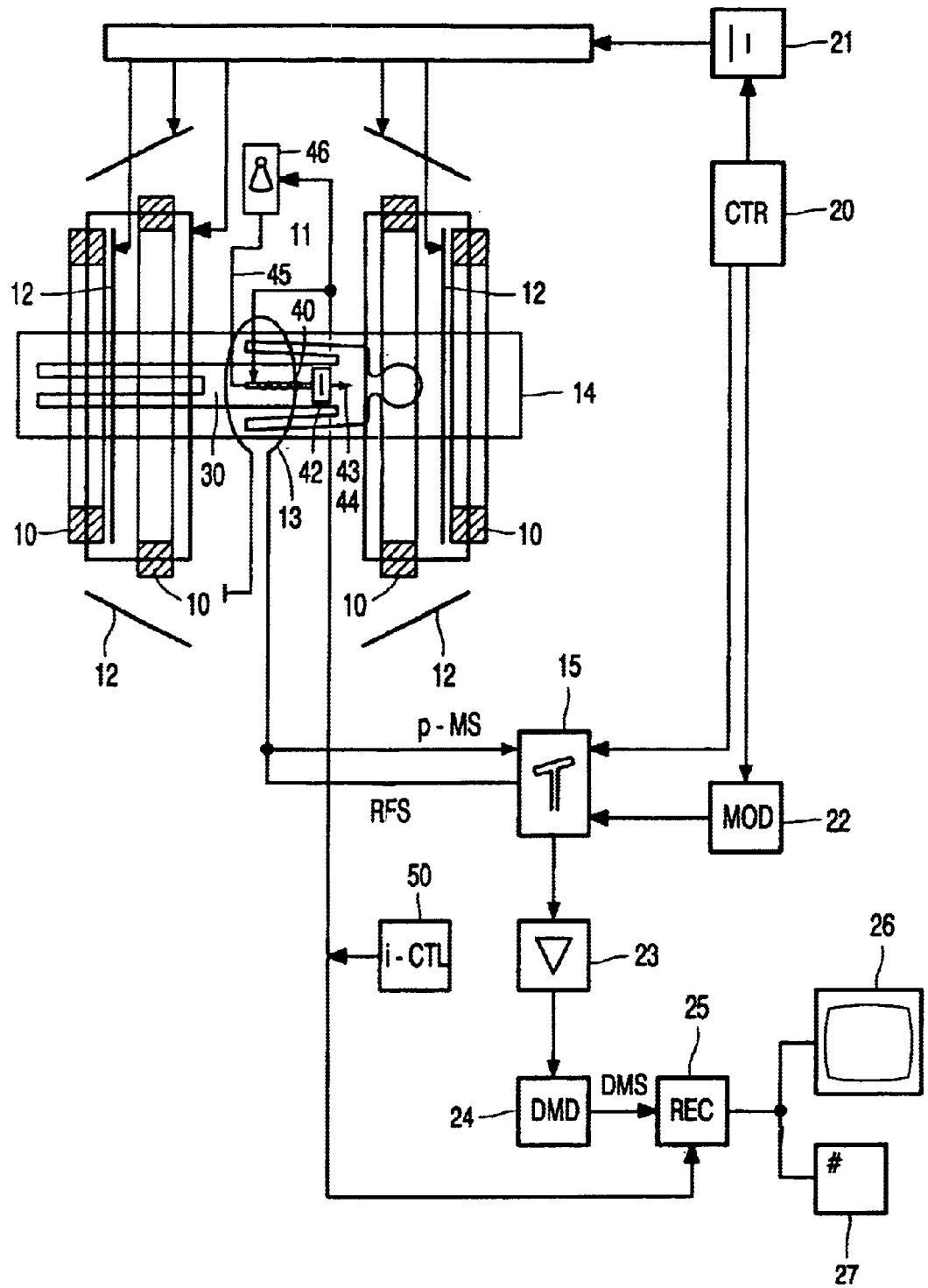
FIG. 1 shows diagrammatically a magnetic resonance imaging system according to the invention.

FIG. 1 shows diagrammatically a magnetic resonance imaging system in which the invention is used. The magnetic resonance imaging system includes a set of main coils 10 for generating the steady, uniform magnetic field. The main coils are constructed in such a manner that they enclose a tunnel-like examination space. The patient to be examined is slid into said tunnel-like examination space. Furthermore, the magnetic resonance imaging system includes a number of gradient coils 11, 12 whereby spatially varying magnetic fields, notably in the form of temporary gradients in different directions, are superposed on the uniform magnetic field. The gradient coils 11, 12 are connected to a variable power supply unit 21. The gradient coils 11, 12 are energized by applying an electrical current thereto by means of the power supply unit 21. The strength, the direction and the duration of the gradients are controlled by control of the power supply unit. The magnetic resonance imaging system also includes transmission and receiving coils 13, 15 for generating the RF excitation pulses and for picking up the magnetic resonance signals, respectively. The transmission coil 13 is preferably constructed as a body coil 13 which is arranged to enclose (a part of) the object to be examined. The body coil is usually mounted in the magnetic resonance imaging system in such a manner that the patient 30 to be examined, being positioned inside the magnetic resonance imaging system, is situated within the body coil 13. The body coil 13 acts as a transmission antenna for the transmission of the RF excitation pulses and RF refocusing pulses. Preferably, the RF pulses transmitted by the body coil 13 have a spatially uniform intensity distribution. The same coil or antenna is usually used alternately as a transmission coil and as a receiving coil. Furthermore, the transmission and receiving coil is usually shaped as a coil, but other geometries where the transmission and receiving coil serves as a transmission and receiving antenna for RF electromagnetic signals are also feasible. The transmission and receiving coil 13 is connected to an electronic transmission/receiving circuit 15.

It is to be noted, however, that separate receiving coils may alternatively be used. Receiving coils in the form of surface coils may be used. Such surface coils have a high sensitivity in a comparatively small volume. The transmission coils, such as the surface coils, are connected to a demodulator 24 and the magnetic resonance signals (RFS) received are demodulated by means of the demodulator 24. The demodulated magnetic resonance signals (DMS) are applied to a reconstruction unit. The receiving coil is connected to a preamplifier 23. The preamplifier 23 amplifies the RF resonance signal (RFS) received by the receiving coil and the amplified RF resonance signal is applied to a demodulator 24. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses. The reconstruction unit derives one or more image signals, representing the image information of the imaged part of the object to be examined, from the demodulated magnetic resonance signals (DMS). In practice the reconstruction unit 25 is preferably constructed as a digital image processing unit 25 which is programmed to derive from the demodulated magnetic resonance signals the image signals which represent the image information of the part of the object to be imaged. The signal on the output of the reconstruction unit is applied to a monitor 26 so as to display the three-dimensional density distribution or the spectroscopic information on the monitor. It is alternatively possible to store the signal from the reconstruction unit in a buffer unit 27 while awaiting further processing.

The magnetic resonance imaging system according to the invention includes a microcoil 40. The microcoil 40 is mounted on an interventional instrument with a catheter 41. The interventional instrument with the microcoil 40 is introduced into the body of the patient 30 with the catheter 41. Relaxation of excited nuclear spins in the vicinity of the microcoil locally produces RF magnetic resonance signals which are received by the microcoil. Such RF magnetic resonance signals are referred to as position magnetic resonance signals (p-MS), because they represent the position of the measuring coil 40 arranged at the measuring site within the body of the patient 30. The microcoil 40 is connected to the reconstruction unit 25, so that the position magnetic resonance signals (p-MS) are applied to the reconstruction unit 25. The reconstruction unit 25 is programmmed so as to reconstruct successive magnetic resonance images from the demodulated magnetic resonance signals (D)MS) on the basis of the position magnetic resonance signals and to correct such magnetic resonance images for any motion in or of the patient.

Furthermore, the interventional instrument includes a temperature sensor 42 for measurement of the local temperature. The interventional instrument is also provided with a so-called "cryoprobe" 43 whereby tissue can be locally and temporarily cooled. Liquid helium can be locally applied. Instead of, or in addition to, a cryoprobe it is also possible to provide the interventional instrument with an optical fiber 45, one end 44 is situated in the immediate vicinity of the microcoil 40. The other end of the optical fiber can be connected to a laser 46. The laser light which then emanates from the end 44 of the optical fiber 45 and enters the patient locally warms up or even heats tissue. An RF ablation probe can also be used to heat tissue. The cryoprobe 43 and/or the laser 46 are controlled by means of an intervention control system 50. The reconstruction unit 25 reconstructs the temperature distribution and/or the variations thereof in the form of one or more thermal images on the basis of the temperature measured by means of the temperature sensor 42, the position magnetic resonance signals (so the position determined for the measuring site) and the demodulated magnetic resonance signals.

Figure 2:
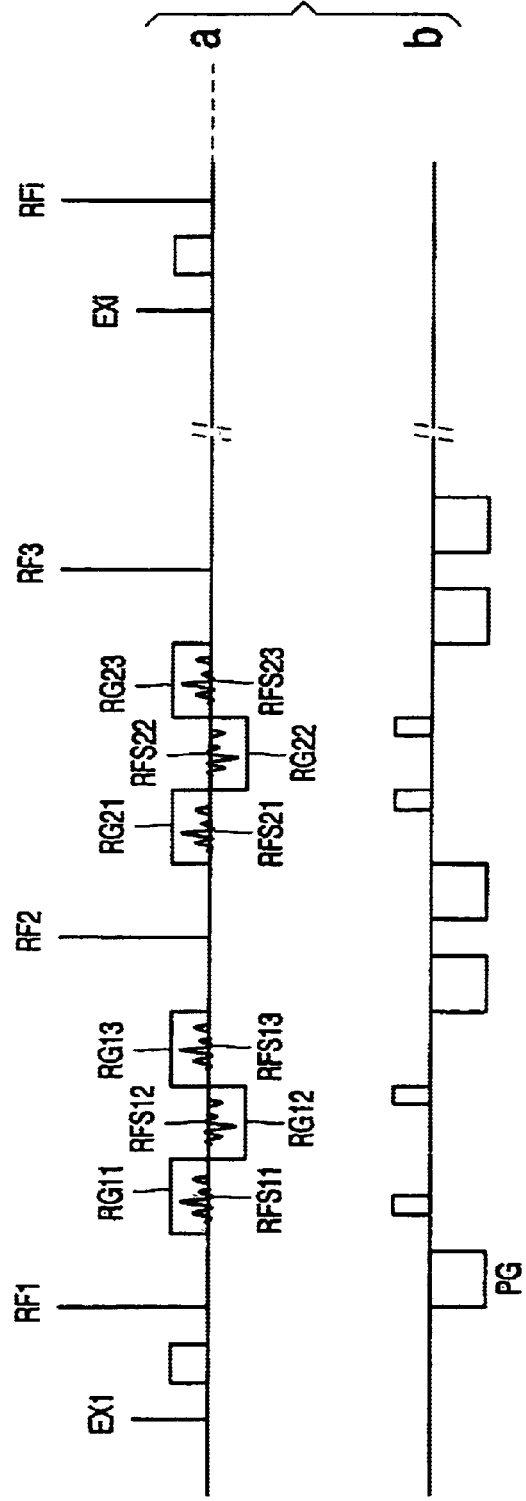
FIG. 2 shows graphically a sequence of RF pulses and gradient pulses used to carry out the invention.
Figure 3:
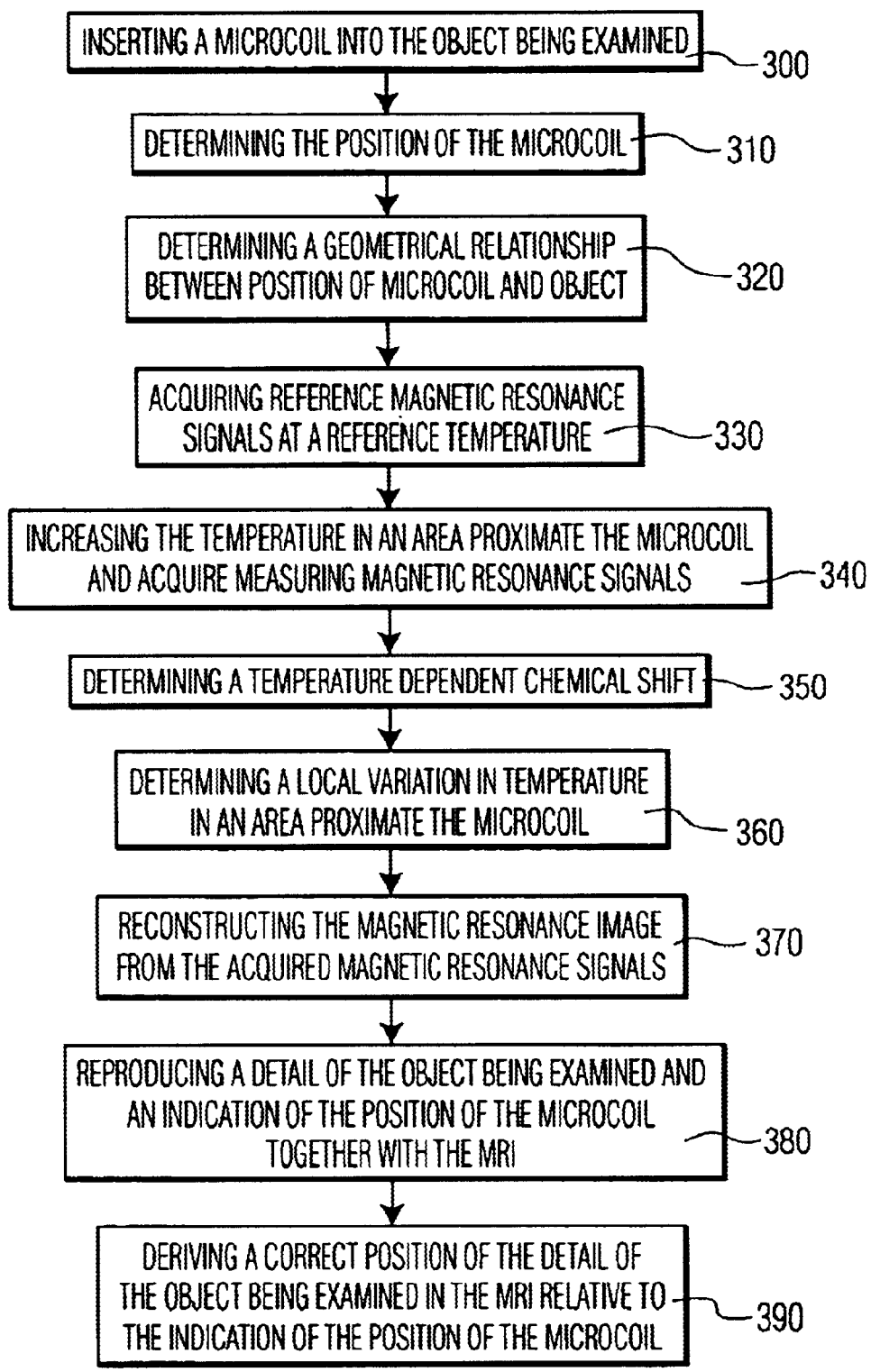
FIG. 3 shows a flow diagram of a method of forming a magnetic resonance image of an object to be examined, according to the invention with the method steps identified as reference numerals 300, 310, 320, 330, 340, 350, 360, 370, 380, and 390.

FIG. 2 shows graphically a sequence of RF pulses and gradient pulses which are used to carry out the invention. Graph (a) shows the sequences of RF excitation pulses (EX1, . . . , EXi), refocusing pulses (RF1, RF2, RF3, . . . , RFi), read-out gradients (RG1, RG2, . . . ) and the magnetic resonance signals (gradient echoes) (RFS11, RFS12, RFS13, RFS21, RFS22, RFS23, . . . ) generated thereby. Graph (b) shows the associated phase encoding gradients. The sequence shown is a so-called GRASE sequence in which a plurality of RF refocusing pulses are applied between individual RF excitation pulses. The RF excitation pulses excite spins in the body of the patient to be examined. The RF excitation pulse excite spins in a selected slice of the body of the patient. Such a slice is selected by superposition of a selection gradient on the steady magnetic field of the main coils. The refocusing pulses generate spin echoes from the excited spins. A plurality of temporary, successive read-out gradients RG11, RG12, . . . , RG23 are applied between successive RF refocusing pulses. The read-out gradients generate the gradient echoes of the excited spins. The combination of the RF refocusing pulses and the read-out gradients yields magnetic resonance signals RFS. Such magnetic resonance signals have the mixed character of spin echo signals and gradient echo signals. Phase-encoding gradients are applied between the successive read-out gradients RG11, . . . , RG23. The direction of the phase-encoding gradients extends essentially perpendicularly to the direction of the read-out gradients. Under the influence of the read-out gradients as shown in the graph (b) in FIG. 2, the wave vector of the magnetic resonance signals describes parallel, mutually offset line segments in the k space. The phase-encoding gradients ensure that path between successive refocusing pulses a part of the k space is traversed each time along a meandering path. The line segments constitute respective straight parts of the meandering path. The successive meandering paths between successive pairs of refocusing pulses are mutually offset in the k space. In the example shown in FIG. 2 a first meandering path in the k space which is described by followed by the magnetic resonance signals RFS11, RFS12 and RFS13 and the meandering path through the k space which is desired by the magnetic resonance signals RFS21, RFS22, RFS23 has been shifted in the direction transversely of the direction of the straight segments of the meandering path.

The invention is used as follows in the GRASE sequence of FIG. 2. Together with the magnetic resonance signals RFS11 . . . RFS13, the microcoil 40 receives position magnetic resonance signals (p-MS) concerning the position of the measuring site which is situated, for example, at the area of the end 45 of the optical fiber. Subsequently, the temperature is locally varied, for example by activation of the laser 46 so that tissue in the vicinity of the end 45 of the fiber is subjected to a thermal treatment. The phase-encoding gradients applied between the successive refocusing pulses RF1 and RF2 can be adapted so as to ensure that the position of the detail, in this case being the treated part of the tissue, is reproduced in the correct location in the magnetic resonance image. In a further elaboration of this implementation of the invention magnetic resonance signals between several pairs of refocusing pulses are used as reference magnetic resonance signals. On the basis of differences between position magnetic resonance signals of the microcoil, acquired between successive pairs of refocusing pulses, it is also possible to detect motion in or of the patient to be examined. On the basis of the differences between position magnetic resonance signals to both sides of a refocusing pulse, subsequently the phase-encoding gradients applied after a next refocusing pulse are adapted so as to correct for the detected motion.

Furthermore, in the GRASE sequence shown in FIG. 2 it is also possible to derive the temperature variation from phase differences between gradient echoes (RF12, RF22, . . . ) which always occur halfway between successive refocusing pulses. The distance in time between successive refocusing pulses is adjusted so that the phase crosses zero halfway between the successive refocusing pulses. A temperature variation causes an additional phase contribution which is approximately proportional to the temperature dependent chemical shift. This phase contribution is exactly the difference between the phases of successive gradient echoes, each time halfway between refocusing pulses.

What is claimed is:

1. A method of forming a magnetic resonance image of an object to be examined, comprising the steps of:
  inserting a microcoil into the object being examined,
  determining the position of the microcoil,
  determining a geometrical relationship between the position of the microcoil and the object being examined,
  acquiring reference magnetic resonance signals at a reference temperature after the microcoil is inserted into the object being examined, after the magnetic resonance signals at the reference temperature are obtained, increasing the temperature in an area proximate the microcoil and acquiring measuring magnetic resonance signals after the temperature in the area proximate the microcoil has been increased, determining a temperature dependent chemical shift upon comparison of the measuring magnetic resonance signals to the reference magnetic resonance signals, determining a local variation in temperature, in the area proximate the microcoil, on the basis of the temperature dependent chemical shift and the determined position of the microcoil, reconstructing the magnetic resonance image from the acquired magnetic resonance signals and on the basis of the determined position of the microcoil, the reconstruction step including reconstructing a reference magnetic resonance image from the reference magnetic resonance signals and reconstructing a measuring magnetic resonance image from the measuring magnetic resonance signals, reproducing a detail of the object being examined and an indication of the position of the microcoil together in the magnetic resonance image, and deriving a correct position of the detail of the object being examined in the magnetic resonance image relative to the indication of the position of the microcoil on the basis of the position of the indication of the position of the microcoil and the determined geometrical relationship between the position of the microcoil and the object being examined.

2. A method of forming a magnetic resonance image as claimed in claim 1, wherein an indication of the position of the microcoil is reproduced in the reference magnetic resonance image and in the measuring magnetic resonance image.

3. A method of forming a magnetic resonance image as claimed in claim 1 further comprising the step of:

making the measuring magnetic resonance image and the reference magnetic resonance image register on the basis of the determined position of the microcoil.

4. A method of forming a magnetic resonance image as claimed in claim 3 further comprising the step on the basis of the determined position of the microcoil, acquiring the reference magnetic resonance signals and the measuring magnetic resonance signals from essentially the same region.

5. A method of forming a magnetic resonance image as claimed in claim 3 further comprising the steps of:

reproducing a detail and an indication of the position of the microcoil in the reference magnetic resonance image, reproducing the same detail and the indication of the position of the microcoil in the measuring magnetic resonance image, and wherein a shift of the detail is derived prom respective positions of the detail relative to the indication of the position of the microcoil in the reference magnetic resonance image and the measuring magnetic resonance image, correcting the position of the detail in the measuring magnetic resonance image is corrected on the basis of the derived shift of the detail.

6. A method of forming a magnetic resonance image as claimed in claim 1, further comprising the step of:

using an energy-dissipating element in conjunction with the microcoil to provide for the increase in temperature in the area proximate the microcoil.

7. A method of forming a magnetic resonance image as claimed in claim 1, further comprising the step of:

arranging an energy-dissipating element near the microcoil to provide for the increase in temperature in the area proximate the microcoil.

8. A method of forming a magnetic resonance image as claimed in claim 1, further comprising the steps of:

inserting an additional microcoil into the object being examined, and measuring the position and direction of a line through the microcoils.

9. A method as claimed in claim 1 wherein the step of determining the position of the microcoil comprises the steps of:

positioning the microcoil at a measuring site such that position magnetic resonance signals are produced by the microcoil, and deriving the position of the microcoil from the position magnetic resonance signals.

10. A method of forming a magnetic resonance image as claimed in claim 1, further comprising the steps of:

inserting two additional microcoils into the object being examined such that all three microcoils are not on the same line, and measuring the position and orientation of a plane through the microcoils.

11. A method of forming a magnetic resonance image as claimed in claim 1, further comprising the steps of:

mounting the microcoil on an interventional instrument.

12. A method of forming a magnetic resonance image as claimed in claim 1, further comprising the step of:

mounting the microcoil on a catheter.

13. A method of forming a magnetic resonance image as claimed in claim 1, wherein the geometrical relationship between the position of the microcoil and the object being examined is determined such that upon movement of the object being examined, an adjusted position of the microcoil is determinable.

* * * * *